US012774364B2

(12) United States Patent
Ferbitz et al.

(10) Patent No.: US 12,774,364 B2
(45) Date of Patent: Oct. 27, 2026

(54) PROCESS FOR PREPARING AT LEAST ONE POLYISOCYANATE

(71) Applicant: BASF SE, Ludwigshafen am Rhein (DE)

(72) Inventors: Jens Ferbitz, Ludwigshafen am Rhein (DE); Jan Pablo Josch, Ludwigshafen am Rhein (DE); Kai Thiele, Antwerp (BE); Torsten Mattke, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 393 days.

(21) Appl. No.: 18/562,515

(22) PCT Filed: May 24, 2022

(86) PCT No.: PCT/EP2022/064007

§ 371 (c)(1),
(2) Date: Nov. 20, 2023

(87) PCT Pub. No.: WO2022/248448

PCT Pub. Date: Dec. 1, 2022

(65) Prior Publication Data

US 2024/0368335 A1 Nov. 7, 2024

(30) Foreign Application Priority Data

May 25, 2021 (EP) .................................... 21175682

(51) Int. Cl.
*C07C 263/10* (2006.01)
*C08G 18/38* (2006.01)
*C08G 18/65* (2006.01)

(52) U.S. Cl.
CPC ........ *C08G 18/6529* (2013.01); *C07C 263/10* (2013.01); *C08G 18/3802* (2013.01)

(58) Field of Classification Search
CPC .................................................... C07C 263/10
See application file for complete search history.

(56) References Cited

U.S. PATENT DOCUMENTS 4,014,914 A 3/1977 Pistor et al.
4,847,408 A 7/1989 Frosch et al.
(Continued)

FOREIGN PATENT DOCUMENTS

CN 1149579 A 5/1997
CN 1290245 A 4/2001
(Continued)

OTHER PUBLICATIONS

International Preliminary Report on Patentability received for PCT Patent Application No. PCT/EP2022/064007, mailed on Dec. 7, 2023, 06 pages.

(Continued)

*Primary Examiner* — Michael L Leonard
(74) *Attorney, Agent, or Firm* — Faegre Drinker Biddle & Reath LLP

(57) ABSTRACT

The present invention relates to a process for preparing at least one polyisocyanate R(—NCO)x, the process comprising preparing a mixture R1 comprising at least one polyamine R(—$NH_2$)x, with x=2 or more, in a first reaction zone Z1; passing at least a portion P1 of the mixture R1, P1 comprising R(—$NH_2$)x, into a storing device D1 and storing P1 in D1 for a period of time Δt1; removing, after storing for Δt1, at least a portion P2 of P1, P2 comprising R(—$NH_2$)x, from D1; passing P2 into a reaction zone Z2; and reacting, in Z2, R(—$NH_2$)x comprised in P2 with phosgene, obtaining a mixture R2 comprising the at least one polyisocyanate R(—NCO)x; wherein Δt1 is in the range of from 1 minute to 7 d.

14 Claims, 2 Drawing Sheets

(56) References Cited

U.S. PATENT DOCUMENTS

| | | | | |
|---|---|---|---|---|
| 6,433,219 | B1 | 8/2002 | Stroefer et al. | |
| 6,472,564 | B1 | 10/2002 | Biskup et al. | |
| 8,436,204 | B2 | 5/2013 | Knoesche et al. | |
| 9,365,503 | B2 * | 6/2016 | Biskup | C07C 263/10 |
| 2004/0171869 | A1 | 9/2004 | Reif et al. | |
| 2004/0260117 | A1 | 12/2004 | Rohde et al. | |
| 2011/0263892 | A1 * | 10/2011 | Breuninger | C07C 265/14 560/347 |
| 2012/0123151 | A1 * | 5/2012 | Bock | C07C 263/10 560/347 |

FOREIGN PATENT DOCUMENTS

| | | | |
|---|---|---|---|
| CN | 1610711 | A | 4/2005 |
| CN | 102282127 | A | 12/2011 |
| EP | 2912010 | B1 | 12/2016 |
| GB | 1037933 | A | 8/1966 |
| WO | 2012/049158 | A1 | 4/2012 |
| WO | 2013/060836 | A1 | 5/2013 |
| WO | 2013/079517 | A1 | 6/2013 |

OTHER PUBLICATIONS

International Search Report and Written Opinion received for PCT Patent Application No. PCT/EP2022/064007, mailed on Aug. 23, 2022, 8 pages.

* cited by examiner

PROCESS FOR PREPARING AT LEAST ONE POLYISOCYANATE

CROSS-REFERENCE TO RELATED APPLICATIONS

This application is a National stage application (under 35 U.S.C. § 371) of PCT/EP2022/064007, filed May 24, 2022, which claims benefit of European Application No. 21175682.0, filed May 25, 2021, both of which are incorporated herein by reference in their entirety.

The present invention relates to a process for preparing at least one polyisocyanate R(—NCO)x, a polyisocyanate R(—NCO)x prepared according to said process and a chemical production unit for carrying out the process for preparing at least one polyisocyanate R(—NCO)x. The present invention further relates to a use of the polyisocyanates R(—NCO)x prepared according to said process.

Polyisocyanates are an important raw material for the production of polyurethanes. These include in particular aromatic di- and polyisocyanates such as TDI and MDI. They are essentially produced by phosgenation of the corresponding polyamines.

The amines are produced in separate plants by hydrogenating nitroaromatics. In the case of MDI, the aniline obtained is condensed in a further stage with, for example, formaldehyde to form polymethylene phenylamines (MDA).

Further, phosgenation is a well-known process for preparing isocyanates. Thereby in liquid phosgenation process the amine is mixed with a solvent and reacted with a phosgene-containing stream to form the isocyanate. After the reaction step hydrogen chloride, excess phosgene and solvent have been separated off, a crude isocyanate product is obtained, which is optionally purified again (TDI) or separated into various types of product (MDI). This is for example disclosed in U.S. Pat. No. 4,847,408 B, US 2004/0260117 A1, and EP 2 912 010 B1.

Furthermore, phosgenations are known in which an amine-containing liquid or gaseous stream and a gaseous phosgene-containing stream are mixed and subsequently reacted, this is disclosed for example in U.S. Pat. No. 8,436,204 B2, WO 2013/060836 A and WO 2013/079517 A.

The quality of the isocyanates products must meet the relevant specifications. Common quality parameters for MDI are the NCO functionality, content of easily and difficultly hydrolyzable chlorine, total chlorine content and color parameters. Such quality parameters depend on the process for preparing isocyanates. Therefore, there is always a need to provide improved process for preparing polyisocyanates which exhibits improved quality parameters, such as decreased easily hydrolysable chlorine (EHC) and high lightness value (L*).

Therefore, it was an object of the present invention to provide an improved process for preparing polyisocyanates which exhibits improved quality parameters, such as decreased easily hydrolysable chlorine (EHC) and high lightness value (L*). Surprisingly, it was found that such polyisocyanates may be obtained by the process of the present invention.

Therefore, the present invention relates to a process for preparing at least one polyisocyanate R(—NCO)x, the process comprising (i) preparing a mixture R1 comprising at least one polyamine R(—$NH_2$)x, with x=2 or more, in a first reaction zone Z1;

(ii) passing at least a portion P1 of the mixture R1, P1 comprising R(—$NH_2$)x, into a storing device D1 and storing P1 in D1 for a period of time Δt1;

(iii) removing, after storing for Δt1, at least a portion P2 of P1, P2 comprising R(—$NH_2$)x, from D1; passing P2 into a reaction zone Z2; and reacting, in Z2, R(—$NH_2$)x comprised in P2 with phosgene, obtaining a mixture R2 comprising the at least one polyisocyanate R(NCO)x;

wherein Δt1 is in the range of from 1 minute to 7 d.

As to (i), it is preferred that the at least one polyamine R(—$NH_2$)x is selected from the group consisting of monomeric methylene diphenylene diamine (mMDA), polymethylene polyphenylene polyamine (pMDA), a mixture of monomer methylene diphenylene diamine and polymethylene polyphenylene polyamine (MDA), tolylenediamine (TDA), isomers of xylylenediamine (XDA), isomers of diaminobenzene, 2,6-xylidine, naphthylene-1,5-diamine (1,5-NDA), 1,4-diaminobutane, 1,5-diaminopentane (PDA), 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4 (or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4(3)-aminomethylcyclohexane (AMCA), 1,3-bis(aminomethyl) cyclohexane, 1,4-bis(aminomethyl)cyclohexane, bis(aminomethyl)norbornane (NBDA), 4,4'-diaminodicyclohexylmethane, 2,4'-diaminodicyclohexylmethane, triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl) hexane and 1,3,5-tris(aminomethyl)cyclohexane. It is more preferred that the at least one polyamine R(—$NH_2$)x is selected from the group consisting of monomeric methylene diphenylene diamine (mMDA), polymethylene polyphenylene polyamine (pMDA), a mixture of monomeric methylene diphenylene diamine and polymethylene polyphenylene polyamine (MDA), and tolylenediamine (TDA).

It is preferred that the at least one polyamine R(—$NH_2$)x is selected from the group consisting of monomeric methylene diphenylene diamine (mMDA), polymethylene polyphenylene polyamine (pMDA), and a mixture of monomeric methylene diphenylene diamine and polymethylene polyphenylene polyamine (MDA), more preferably selected from the group consisting of monomeric methylene diphenylene diamine (mMDA) and a mixture of monomeric methylene diphenylene diamine and polymethylene polyphenylene polyamine (MDA).

Preferably the monomeric methylene diphenylene diamine (mMDA) comprises, more preferably consists of, one or more 4,4'-diaminodiphenylmethane, 2,2'-diaminodiphenylmethane and 2,4'-diaminodiphenylmethane. It is more preferred that the at least one polyamine R(—$NH_2$)x is 4,4'-diaminodiphenylmethane. Therefore, the present invention preferably relates to a process for preparing at least one polyisocyanate R(—NCO)x, with x=2 or more, the process comprising (i) preparing a mixture R1 comprising 4,4'-diaminodiphenylmethane, in a first reaction zone Z1;

(ii) passing at least a portion P1 of the mixture R1, P1 comprising the 4,4'-diaminodiphenylmethane, into a storing device D1 and storing P1 in D1 for a period of time Δt1;

(iii) removing, after storing for Δt1, at least a portion P2 of P1, P2 comprising the 4,4'-diaminodiphenylmethane, from D1; passing P2 into a reaction zone Z2; and reacting, in Z2, the 4,4'-diaminodiphenylmethane comprised in P2 with phosgene, obtaining a mixture R2 comprising the at least one corresponding polyisocyanate R(—NCO)x;

wherein Δt1 is in the range of from 1 minute to 7 d.

Alternatively, it is preferred that the at least one polyamine R(—$NH_2$)x is a mixture of monomeric methylene diphenylene diamine and polymethylene polyphenylene polyamine (MDA). Therefore, the present invention preferably relates to a process for preparing at least one polyisocyanate R(—NCO)x, the process comprising (i) preparing a mixture R1 comprising a mixture of monomeric methylene diphenylene diamine and polymethylene polyphenylene polyamine (MDA), in a first reaction zone Z1;

(ii) passing at least a portion P1 of the mixture R1, P1 comprising the MDA, into a storing device D1 and storing P1 in D1 for a period of time Δt1;

(iii) removing, after storing for Δt1, at least a portion P2 of P1, P2 comprising the MDA, from D1; passing P2 into a reaction zone Z2; and reacting, in Z2, the MDA comprised in P2 with phosgene, obtaining a mixture R2 comprising the at least one polyisocyanate R(NCO)x, being more preferably MDI;

wherein Δt1 is in the range of from 1 minute to 7 d.

Alternatively, it is preferred that the at least one polyamine R(—$NH_2$)x is tolylenediamine (TDA).

Therefore, the present invention preferably relates to a process for preparing at least one polyisocyanate R(—NCO)x, the process comprising (i) preparing a mixture R1 comprising tolylenediamine (TDA), in a first reaction zone Z1;

(ii) passing at least a portion P1 of the mixture R1, P1 comprising the TDA, into a storing device D1 and storing P1 in D1 for a period of time Δt1;

(iii) removing, after storing for Δt1, at least a portion P2 of P1, P2 comprising the TDA, from D1; passing P2 into a reaction zone Z2; and reacting, in Z2, the TDA comprised in P2 with phosgene, obtaining a mixture R2 comprising the at least one polyisocyanate R(—NCO)x, being more preferably TDI;

wherein Δt1 is in the range of from 1 minute to 7 d.

In the context of the present invention, it is preferred that from 95 to 100 weight-%, more preferably from 98 to 100 weight-%, more preferably from 99 to 100 weight-%, more preferably from 99.5 to 100 weight-%, of the mixture R1 consists of the at least one polyamine R(—$NH_2$)x.

It is preferred that from 95 to 100 weight-%, more preferably from 98 to 100 weight-%, more preferably from 99 to 100 weight-%, more preferably from 99.5 to 100 weight-%, of the mixture R1 consists of monomeric methylene diphenylene diamine (mMDA), more preferably 4,4'-diaminodiphenylmethane. It is alternatively preferred that from 95 to 100 weight-%, more preferably from 98 to 100 weight-%, more preferably from 99 to 100 weight-%, more preferably from 99.5 to 100 weight-%, of the mixture R1 consists of MDA, namely a mixture of monomeric methylene diphenylene diamine and polymethylene polyphenylene polyamine. It is alternatively preferred that from 95 to 100 weight-%, more preferably from 98 to 100 weight-%, more preferably from 99 to 100 weight-%, more preferably from 99.5 to 100 weight-%, of the mixture R1 consists of tolylenediamine (TDA), more preferably a mixture of 2,4-diaminotoluene (80 weight-%) and 2,6-diaminotoluene (20 weight-%).

As to the preparation of the mixture R1 comprising at least one polyamine R(—$NH_2$)x according to (i), it is noted that any process known in the art can be used. For example, such a process is disclosed in WO 2017/125302 A1.

As to (i), it is preferred according to the present invention that it comprises (i.1) reacting primary amines with an aldehyde compound in presence of an acid in a first reaction zone Z1, obtaining a mixture R0 comprising the primary amines and at least one polyamine R(—$NH_2$)x, with x=2 or more;

(i.2) separating the primary amines from the at least one polyamine R(—$NH_2$)x comprised in the mixture R0 obtained in (i.1), obtaining a mixture R1 comprising at least one polyamine R($NH_2$)x.

Preferably the primary amines in (i.1) are aniline. Alternatively, different starting amines can be used depending on the polyamine the skilled person would like to obtain in (i). Processes for preparing polyamine are detailed in the art.

Preferably the aldehyde compound in (i.1) is formaldehyde.

Preferably the acid in (i.1) is one or more of hydrochloric acid, sulphuric acid and phosphoric acid, more preferably hydrochloric acid.

In the context of the present invention, it is preferred that the portion P1 has the same chemical and physical composition as R1 and the portion P2 has the same chemical and physical composition as P1.

It is however noted that for example in case the mixture R1 is prepared with different ratios of primary amines to aldehyde over the time compared to at the start of the process, the resulting polyamine in the portion P1 would be different when entering the storing device compared to the polyamine present initially.

In the context of the present invention, it is preferred that the storing device D1 according to (ii) is one or more storing tanks. Preferably the storing tanks are made of one or more of carbon steel, duplex steel and stainless steel.

Preferably storing P1 in D1 according to (ii) is performed in the dark.

Preferably storing P1 in D1 according to (ii) is performed under a gas atmosphere, the gas atmosphere being an inert gas, more preferably nitrogen. Without wanting to be bound to any theory, it is believed that this would prevent for example the coloring of the mixture R1 comprising at least one polyamine. In the context of the present invention, the expression “under a gas atmosphere” can be used interchangeably with the expression “in a gas atmosphere”.

Preferably, in D1, the temperature of the liquid phase of P1, T(P1), in ° C., is above the melting point of the at least one polyamine R(—$NH_2$)x comprised in P1, M(P1), in ° C., more preferably T(P1)≥5° C.+M(P1), more preferably T(P1)≥20° C.+M(P1).

Preferably, M(P1) is 80° C., and, in D1, T(P1)≥85° C., more preferably T(P1)≥100° C. It is more preferred that, in D1, 120° C.≤T(P1)≤190° C., more preferably 130° C.≤T(P1)≤180° C., more preferably 135° C.≤T(P1)≤175° C., more preferably 140° C.≤T(P1)≤170° C.

Preferably, when the at least one polyamine R(—$NH_2$)x is MDA, M(P1) is 80° C., and, in D1, T(P1)≥85° C., more preferably T(P1)≥100° C. It is more preferred, when the at least one polyamine R(—$NH_2$)x is MDA, that, in D1, 120° C.≤T(P1)≤190° C., more preferably 130° C.≤T(P1)≤170° C., more preferably 135° C.≤T(P1)≤145° C.

Preferably, when the at least one polyamine R(—$NH_2$)x is TDA, M(P1) is 100° C., and, in D1, T(P1)≥105° C. It is more preferred, when the at least one polyamine R(—$NH_2$)x is TDA, that, in D1, T(P1)≥120° C., more preferably 120° C.≤T(P1)≤180° C., more preferably 125° C.≤T(P1)≤150° C., more preferably 125° C.≤T(P1)≤135° C.

Preferably the storing device D1 is ventilated with a gas atmosphere, more preferably the gas atmosphere being an inert gas, more preferably nitrogen.

As to the pressure in the storing device D1, it is preferred that it is in the range of from 0.5 to 2, bar (abs), more preferably in the range of from 0.8 to 1.3 bar (abs), more preferably in the range of from 1 bara to 1.1 bar (abs).

Preferably Δt1 is in the range of from 15 minutes to 6 d, more preferably in the range of from 45 minutes to 5 d, more preferably in the range of from 1 h to 4 d.

It is more preferred that Δt1 is in the range of from 2 h to 3 d, more preferably in the range of from 5 h to 1 d, more preferably in the range of from 7 h to 20 h, more preferably in the range of from 8 h to 16 h.

Preferably removing at least a portion P2 of P1 according to (iii) comprises pumping the at least one portion P2 from the storing device D1.

As to the preparation of the mixture R2 comprising at least one polyamine R(—$NH_2$)x according to (iii), it is noted that any process known in the art can be used. For example, such a process is disclosed in WO2013/060836 A1.

It is preferred that reacting, in Z2, the at least one polyamine R(—$NH_2$)x comprised in P2 with phosgene according to (iii) comprises admixing a solvent to the at least one polyamine R(—$NH_2$)x comprised in P2, more preferably at a temperature in the range of from 50 to 180° C., more preferably in the range of from 70 to 140° C., more preferably in the range of from 80 to 120° C., obtaining a polyamine mixture;

contacting the polyamine mixture with phosgene in the reaction zone Z2 and heating the obtained mixture to a temperature in the range of from 90 to 140° C., more preferably in the range of from 110 to 130° C., obtaining the mixture R2.

It is preferred that admixing the solvent to the at least one polyamine R(—$NH_2$)x comprised in P2 be performed with a static mixer.

Preferably the solvent is selected from the group consisting of monochlorobenzene, toluene, o- or p-dichlorobenzene, trichlorobenzene, chlorotoluene, chloroxylene, chloroethylbenzene, chloronaphthalene, chlorodiphenyl, xylene, decahydronaphthalene, benzene and a mixture of two or more thereof, more preferably selected from the group consisting of monochlorobenzene, toluene and o-dichlorobenzene, more preferably monochlorobenzene.

It is preferred that the reaction zone Z2 comprises a reactor, wherein the reactor is more preferably one or more of stirred vessels, plug-flow reactor and reaction columns.

It is preferred that the process further comprises (iv) purifying the mixture R2 obtained according to (iii), R2 comprising the at least one polyisocyanate R(—NCO)x and one or more of phosgene, hydrogen chloride, and portion of the solvent, obtaining a purified mixture R2(p).

Preferably purifying the mixture R2 according to (iv) comprises removing one or more of phosgene, hydrogen chloride and a portion of the solvent, more preferably removing phosgene, hydrogen chloride and a portion of the solvent, from R2.

It is preferred that the process further comprises (v) removing the solvent from the purified mixture R2(p) obtained according to (iv), obtaining a mixture R3 comprising the at least one polyisocyanate R(—NCO)x, wherein from 80 to 100 weight-%, more preferably from 85 to 99 weight-%, more preferably from 90 to 98 weight-%, of the mixture R3 consist of the at least one polyisocyanate R(—NCO)x.

It is preferred that from 80 to 100 weight-%, more preferably from 85 to 99 weight-%, more preferably from 90 to 98 weight-%, of the mixture R3 consist of monomeric methylene diphenylene diisocyanate (mMDI), more preferably 4,4'-methylene (diphenyl diisocyanate). Alternatively, it is preferred that from 80 to 100 weight-%, more preferably from 85 to 99 weight-%, more preferably from 90 to 98 weight-%, of the mixture R3 consist of MDI, namely a mixture of monomeric methylene diphenylene diisocyanate and polymethylene polyphenylene polyisocyanate. Alternatively, it is preferred that from 80 to 100 weight-%, more preferably from 85 to 99 weight-%, more preferably from 90 to 98 weight-%, of the mixture R3 consist of tolylene diisocyanate (TDI), more preferably a mixture of 2,4-TDI (80 weight-%) and 2,6-TDI (20 weight-%).

Preferably the process of the present invention consists of (i), (ii) and (iii), more preferably of (i), (ii), (iii) and (iv), more preferably of (i), (ii), (iii), (iv) and (v).

The present invention further relates to a polyisocyanate R(—NCO)x, with x=2 or more, obtainable or obtained according to a process according to the present invention for use in a process for preparing polyurethanes.

Preferably the polyisocyanate R(—NCO)x has a NCO functionality of 2 or more, more preferably of 2 or 3, more preferably of 2.

It is preferred that x=2.

Preferably the polyisocyanate R(—NCO)x is selected from the group consisting of monomeric methylene diphenylene diisocyanate (mMDI), polymethylene polyphenylene polyisocyanate (pMDI), a mixture of monomeric methylene diphenylene diisocyanate and polymethylene polyphenylene polyisocyanate (MDI), tolylene diisocyanate (TDI), isomers of xylylene diisocyanate (XDI), isomers of diisocyanatobenzene, xylene 2,6-isocyanate, naphthylene 1,5-diisocyanate (1,5-NDI), 1,4-diisocyanate, pentane 1,5-diisocyanate (PDI), hexane 1,6-diisocyanate (HDI), octane 1,8-diisocyanate, nonane 1,9-diisocyanate, decane, 1,10-diisocyanate, 2,2-dimethylpentane 1,5-diisocyanate, 2-methylpentane 1,5-diisocyanate (MPDI), 2,4,4 (or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3-bis(isocyanatomethyl) cyclohexane, 1,4-bis(isocyanatomethyl)cyclohexane, bis (isocyanatomethyl)norbornane (NBDI), 4,4'-diisocyanatodicyclohexylmethane, 2,4'-diisocyanatodicyclohexylmethane, triisocyanatocyclohexane, tris(isocyanatomethyl) cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl) heptane, 1,6-diisocyanato-3-(isocyanatomethyl)hexane and 1,3,5-tris(isocyanatomethyl)cyclohexane, more preferably selected from the group consisting of monomeric methylene diphenylene diisocyanate (mMDI), polymethylene polyphenylene polyisocyanate (pMDI), a mixture of monomer methylene diphenylene diisocyanate and polymethylene polyphenylene polyisocyanate (MDI), and tolylene diisocyanate (TDI).

It is preferred that the polyisocyanate R(—NCO)x is selected from the group consisting of monomeric methylene diphenylene diisocyanate (mMDI), polymethylene polyphenylene polyisocyanate (pMDI) and a mixture of monomeric methylene diphenylene diisocyanate and polymethylene polyphenylene polyisocyanate (MDI), more preferably selected from the group consisting of monomeric methylene diphenylene diisocyanate (mMDI) and a mixture of monomeric methylene diphenylene diisocyanate and polymethylene polyphenylene polyisocyanate (MDI).

Preferably the monomeric methylene diphenylene diisocyanate (mMDI) comprises, more preferably consists of, one or more 4,4'-methylene (diphenyl diisocyanate) (4,4'-MDI), 2,2'-methylene (diphenyl diisocyanate) (2,2'-MDI) and 2,4'-methylene (diphenyl diisocyanate) (2,4'-MDI), more preferably 4,4'-methylene (diphenyl diisocyanate) (4,4'-MDI). It is more preferred that the polyisocyanate R(—NCO)x is a monomeric methylene diphenylene diisocyanate (mMDI) which comprises, more preferably consists of, one or more 4,4'-methylene (diphenyl diisocyanate) (4,4'-MDI), 2,2'-methylene (diphenyl diisocyanate) (2,2'-MDI) and 2,4'-methylene (diphenyl diisocyanate) (2,4'-MDI), more preferably 4,4'-methylene (diphenyl diisocyanate) (4,4'-MDI). It is more preferred that the polyisocyanate R(—NCO)x is 4,4'-methylene (diphenyl diisocyanate) (4,4'-MDI).

Alternatively, it is preferred that the polyisocyanate R(—NCO)x is MDI, namely a mixture of monomeric methylene diphenylene diisocyanate and polymethylene polyphenylene polyisocyanate.

Alternatively, it is preferred that the polyisocyanate R(—NCO)x is TDI, namely a mixture of 2,4-TDI (80 weight-%) and 2,6-TDI (20 weight-%).

In the context of the present invention, it is preferred that the polyisocyanate R(—NCO)x has a NCO content in the range of from 10 to 60 weight-%, more preferably in the range of from 20 to 55 weight-%, based on the total weight of the polyisocyanate.

It is more preferred that the polyisocyanate R(—NCO)x has a NCO content in the range of from 25 to 35 weight-%, preferably in the range of from 30 to 35 weight-%, based on the total weight of the polyisocyanate.

It is preferred that the polyisocyanate R(—NCO)x is MDI, namely a mixture of monomeric methylene diphenylene diisocyanate and polymethylene polyphenylene polyisocyanate, and that it has a NCO content in the range of from 25 to 34 weight-%, preferably in the range of from 30 to 33.6 weight-%, based on the total weight of the polyisocyanate.

It is preferred that the polyisocyanate R(—NCO)x comprises a content of easily hydrolysable chlorine (EHC) of at most 500 mg/kg, more preferably of at most 450 mg/kg, more preferably of at most 400 mg/kg, the EHC being preferably determined according to ASTM D4667-87.

It is preferred that the polyisocyanate R(—NCO)x is MDI, namely a mixture of monomeric methylene diphenylene diisocyanate and polymethylene polyphenylene polyisocyanate, and that it comprises a content of easily hydrolysable chlorine (EHC) of at most 500 mg/kg, more preferably of at most 450 mg/kg, more preferably of at most 400 mg/kg, the EHC being preferably determined according to ASTM D4667-87.

It is preferred that the polyisocyanate R(—NCO)x has a brightness value L* of at least 40, more preferably in the range of from 40 to 100, more preferably in the range of from 45 to 99, more preferably in the range of 55 to 98, more preferably in the range of from 75 to 95, the brightness value L* being preferably determined according to ASTM D7133-16.

It is preferred that the polyisocyanate R(—NCO)x is 4,4'-MDI and that it has a brightness value L* of at least 40, more preferably in the range of from 40 to 100, more preferably in the range of from 45 to 99, more preferably in the range of from 45 to 80, the brightness value L* being preferably determined according to ASTM D7133-16.

It is preferred that the polyisocyanate R(—NCO)x is MDI (the mixture as defined in the foregoing) and that it has a brightness value L* of at least 40, more preferably in the range of from 40 to 100, more preferably in the range of from 45 to 99, more preferably in the range of 55 to 98, more preferably in the range of from 75 to 95, the brightness value L* being preferably determined according to ASTM D7133-16.

It is preferred that, when the polyisocyanate is TDI (the mixture as defined in the foregoing), said polyisocyanate has a NCO content in the range of from 40 to 50 weight-%, more preferably in the range of from 45 to 50 weight-%, based on the total weight of the polyisocyanate. It is preferred that the polyisocyanate is TDI, namely a mixture of 2,4-TDI (80 weight-%) and 2,6-TDI (20 weight-%).

It is preferred that the polyisocyanate R(—NCO)x is TDI (the mixture as defined in the foregoing) and that it has a brightness value L* of at least 40, more preferably in the range of from 40 to 100, more preferably in the range of from 45 to 99, more preferably in the range of 55 to 98, more preferably in the range of from 75 to 95, the brightness value L* being preferably determined according to ASTM D7133-16.

The present invention further relates to a use of at least one polyisocyanate R(—NCO)x, with x=2 or more, according to the present invention, for preparing polyurethanes.

The present invention further relates to a chemical production unit for carrying out the process for preparing at least one polyisocyanate R(—NCO)x according to the present invention, comprising

- a reaction zone Z1 for preparing the at least one polyamines R(—$NH_2$)x, with x=2 or more, comprising
  - a reaction means for preparing a mixture R1;
  - a means for removing at least a portion P1 of the mixture R1 from the reaction zone Z1;
- a storing device D1 for storing P1 for a period of time Δt1, wherein Δt1 is in the range of from 1 minute to 7 d;
- a means for removing at least a portion P2 of P1, P2 comprising R(—$NH_2$)x, from D1;
- a reaction zone Z2 for preparing the at least one polyisocyanate R(—NCO)x comprising
  - a reaction means for reacting P2 with phosgene and obtaining a mixture R2.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 5", every embodiment in this range is meant to be explicitly disclosed for the skilled person, i.e. the wording of this term is to be understood by the skilled person as being synonymous to "The process of any one of embodiments 1, 2, 3, 4 and 5". Further, it is explicitly noted that the following set of embodiments represents a suitably structured part of the general description directed to preferred aspects of the present invention, and, thus, suitably supports, but does not represent the claims of the present invention.

1. A process for preparing at least one polyisocyanate R(—NCO)x, the process comprising
   (i) preparing a mixture R1 comprising at least one polyamine R(—$NH_2$)x, with x=2 or more, in a first reaction zone Z1;
   (ii) passing at least a portion P1 of the mixture R1, P1 comprising R(—$NH_2$)x, into a storing device D1 and storing P1 in D1 for a period of time Δt1;
   (iii) removing, after storing for Δt1, at least a portion P2 of P1, P2 comprising R(—$NH_2$)x, from D1; passing P2 into a reaction zone Z2; and reacting, in Z2, R(—$NH_2$)x comprised in P2 with phosgene, obtaining a mixture R2 comprising the at least one polyisocyanate R(—NCO)x;

wherein Δt1 is in the range of from 1 minute to 7 d.
2. The process of embodiment 1, wherein the at least one polyamine R(—$NH_2$)x is selected from the group consisting of monomeric methylene diphenylene diamine (mMDA), polymethylene polyphenylene polyamine (pMDA), a mixture of monomer methylene diphenylene diamine and polymethylene polyphenylene polyamine (MDA), tolylenediamine (TDA), isomers of xylylenediamine (XDA), isomers of diaminobenzene, 2,6-xylidine, naphthylene-1,5-diamine (1,5-NDA), 1,4-diaminobutane, 1,5-diaminopentane (PDA), 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4 (or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4(3)-aminomethylcyclohexane (AMCA), 1,3-bis(aminomethyl)cyclohexane, 1,4-bis (aminomethyl)cyclohexane, bis(aminomethyl)norbornane (NBDA), 4,4'-diaminodicyclohexylmethane, 2,4'-diaminodicyclohexylmethane, triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl) heptane, 1,6-diamino-3-(aminomethyl)hexane and 1,3,5-tris(aminomethyl)cyclohexane, preferably is selected from the group consisting of monomeric methylene diphenylene diamine (mMDA), polymethylene polyphenylene polyamine (pMDA), a mixture of monomeric methylene diphenylene diamine and polymethylene polyphenylene polyamine (MDA), and tolylenediamine (TDA).
3. The process of embodiment 2, wherein the at least one polyamine R(—$NH_2$)x is selected from the group consisting of monomeric methylene diphenylene diamine (mMDA), polymethylene polyphenylene polyamine (pMDA), and a mixture of monomeric methylene diphenylene diamine and polymethylene polyphenylene polyamine (MDA), preferably selected from the group consisting of monomeric methylene diphenylene diamine (mMDA) and a mixture of monomeric methylene diphenylene diamine and polymethylene polyphenylene polyamine (MDA).
4. The process of embodiment 3 or 4, wherein the monomeric methylene diphenylene diamine (mMDA) comprises, preferably consists of, one or more 4,4'-diaminodiphenylmethane, 2,2'-diaminodiphenylmethane and 2,4'-diaminodiphenylmethane.
5. The process of embodiment 4, wherein the at least one polyamine R(—$NH_2$)x is 4,4'-diaminodiphenylmethane.
6. The process of any one of embodiments 1 to 5, wherein from 95 to 100 weight-%, preferably from 98 to 100 weight-%, more preferably from 99 to 100 weight-%, more preferably from 99.5 to 100 weight-%, of the mixture R1 consists of the at least one polyamine R($NH_2$)x.
7. The process of any one of embodiments 1 to 6, wherein the portion P1 has the same chemical and physical composition as R1 and the portion P2 has the same chemical and physical composition as P1.
8. The process of any one of embodiments 1 to 7, wherein (i) comprises
   (i.1) reacting primary amines with an aldehyde compound in presence of an acid in a first reaction zone Z1, obtaining a mixture R0 comprising the primary amines and at least one polyamine R(—$NH_2$)x, with x=2 or more;
   (i.2) separating the primary amines from the at least one polyamine R(—$NH_2$)x comprised in the mixture R0 obtained in (i.1), obtaining a mixture R1 comprising at least one polyamine R(—$NH_2$)x.
9. The process of embodiment 8, as far as embodiment 8 depends on any one of embodiments 3 to 5, wherein the primary amines in (i.1) are aniline.
10. The process of embodiment 8 or 9, as far as embodiment 8 depends on any one of embodiments 3 to 5, wherein the aldehyde compound in (i.1) is formaldehyde.
11. The process of any one of embodiments 8 to 10, as far as embodiment 8 depends on any one of embodiments 3 to 5, wherein the acid in (i.1) is one or more of hydrochloric acid, sulphuric acid and phosphoric acid, preferably hydrochloric acid.
12. The process of any one of embodiments 1 to 11, wherein the storing device D1 according to (ii) is one or more storing tanks.
13. The process of any one of embodiments 1 to 12, wherein storing P1 in D1 according to (ii) is performed in the dark.
14. The process of any one of embodiments 1 to 13, wherein storing P1 in D1 according to (ii) is performed under a gas atmosphere, the gas atmosphere being an inert gas, preferably nitrogen.
15. The process of any one of embodiments 1 to 14, wherein, in D1, the temperature of the liquid phase of P1, T(P1), in ° C., is above the melting point of the at least one polyamine R(—$NH_2$)x comprised in P1, M(P1), in ° C., preferably T(P1)≥5° C.+M(P1), more preferably T(P1)≥20° C.+M(P1).
16. The process of embodiment 15, wherein M(P1) is 80° C., and, in D1, T(P1)≥85° C., wherein preferably T(P1)≥100° C., wherein more preferably 120° C.≤T(P1)≤190° C., wherein more preferably 130° C.≤T(P1)≤180° C., wherein more preferably 135° C.≤T(P1)≤175° C., more preferably 140° C.≤T(P1)≤170° C.
17. The process of embodiment 15, when the at least one polyamine R(—$NH_2$)x is TDA, wherein M(P1) is 100° C., and, in D1, T(P1)≥105° C., wherein preferably T(P1)≥120° C., wherein more preferably 120° C.≤T(P1)≤180° C., wherein more preferably 125° C.≤T(P1)≤150° C.
18. The process of any one of embodiments 1 to 17, wherein the storing device D1 is ventilated with a gas atmosphere, preferably wherein the gas atmosphere is an inert gas, more preferably nitrogen.

19. The process of any one of embodiments 1 to 18, wherein the pressure in the storing device D1 is in the range of from 0.5 to 2 bar (abs) preferably in the range of from 0.8 to 1.3 bar (abs), more preferably in the range of from 1 bara to 1.1 bar (abs).
20. The process of any one of embodiments 1 to 19, wherein Δt1 is in the range of from 15 minutes to 6 d, preferably in the range of from 45 minutes to 5 d, more preferably in the range of from 1 h to 4 d.
21. The process of embodiment 20, wherein Δt1 is in the range of from 2 h to 3 d, preferably in the range of from 5 h to 1 d, more preferably in the range of from 7 h to 20 h, more preferably in the range of from 8 h to 16 h.
22. The process of any one of embodiments 1 to 21, wherein removing at least a portion P2 of P1 according to (iii) comprises pumping the at least one portion P2 from the storing device D1.
23. The process of any one of embodiments 1 to 22, wherein reacting, in Z2, the at least one polyamine R(—$NH_2$)x comprised in P2 with phosgene according to (iii) comprises
    admixing a solvent to the at least one polyamine R(—$NH_2$)x comprised in P2, and stirring, preferably at a temperature in the range of from 50 to 180° C., more preferably in the range of from 70 to 140° C., more preferably in the range of from 80 to 120° C., obtaining a polyamine mixture;
    contacting the polyamine mixture with phosgene in the reaction zone Z2 and heating the obtained mixture to a temperature in the range of from 90 to 140° C., preferably in the range of from 110 to 130° C., obtaining the mixture R2.
24. The process of embodiment 23, wherein the solvent is selected from the group consisting of monochlorobenzene, toluene, o- or p-dichlorobenzene, trichlorobenzene, chlorotoluene, chloroxylene, chloroethylbenzene, chloronaphthalene, chlorodiphenyl, xylene, decahydronaphthalene, benzene and a mixture of two or more thereof, preferably selected from the group consisting of monochlorobenzene, toluene and o-dichlorobenzene, more preferably monochlorobenzene.
26. The process of any one of embodiments 1 to 25, wherein the reaction zone Z2 comprises a reactor, wherein the reactor preferably is one or more of stirred vessels, plug-flow reactor and reaction columns.
27. The process of any one of embodiments 1 to 26, further comprising
    (iv) purifying the mixture R2 obtained according to (iii), R2 comprising the at least one polyisocyanate R(—NCO)x and one or more of phosgene, hydrogen chloride, and portion of the solvent, obtaining a purified mixture R2(p).
28. The process of embodiment 27, wherein purifying the mixture R2 according to (iv) comprises removing one or more of phosgene, hydrogen chloride and a portion of the solvent, preferably removing phosgene, hydrogen chloride and a portion of the solvent, from R2.
29. The process of embodiment 27 or 28, further comprising
    (v) removing the solvent from the purified mixture R2(p) obtained according to (iv), obtaining a mixture R3 comprising the at least one polyisocyanate R(—NCO)x, wherein from 80 to 100 weight-%, preferably from 85 to 99 weight-%, more preferably from 90 to 98 weight-%, of the mixture R3 consist of the at least one polyisocyanate R(—NCO)x.
30. The process of any one of embodiments 1 to 29, consisting of (i), (ii) and (iii), preferably (i), (ii), (iii) and (iv), more preferably (i), (ii), (iii), (iv) and (v).
31. Polyisocyanate R(—NCO)x, with x=2 or more, obtainable or obtained according to a process according to any one of embodiments 1 to 30 for use in a process for preparing polyurethanes.
32. The polyisocyanate of embodiment 31, having a NCO functionality of 2 or more, preferably of 2 or 3, more preferably of 2. (x=2)
33. The polyisocyanate of embodiment 31 or 32, being selected from the group consisting of monomeric methylene diphenylene diisocyanate (mMDI), polymethylene polyphenylene polyisocyanate (pMDI), a mixture of monomeric methylene diphenylene diisocyanate and polymethylene polyphenylene polyisocyanate (MDI), tolylene diisocyanate (TDI), isomers of xylylene diisocyanate (XDI), isomers of diisocyanatobenzene, xylene 2,6-isocyanate, naphthylene 1,5-diisocyanate (1,5-NDI), 1,4-diisocyanate, pentane 1,5-diisocyanate (PDI), hexane 1,6-diisocyanate (HDI), octane 1,8-diisocyanate, nonane 1,9-diisocyanate, decane, 1,10-diisocyanate, 2,2-dimethylpentane 1,5-diisocyanate, 2-methylpentane 1,5-diisocyanate (MPDI), 2,4,4 (or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3-bis(isocyanatomethyl) cyclohexane, 1,4-bis(isocyanatomethyl)cyclohexane, bis(isocyanatomethyl)norbornane (NBDI), 4,4'-diisocyanatodicyclohexylmethane, 2,4'-diisocyanatodicyclohexylmethane, triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl) heptane, 1,6-diisocyanato-3-(isocyanatomethyl)hexane and 1,3,5-tris(isocyanatomethyl)cyclohexane, preferably selected from the group consisting of monomeric methylene diphenylene diisocyanate (mMDI), polymethylene polyphenylene polyisocyanate (pMDI), a mixture of monomer methylene diphenylene diisocyanate and polymethylene polyphenylene polyisocyanate (MDI), and tolylene diisocyanate (TDI).
34. The polyisocyanate of embodiment 33, is selected from the group consisting of monomeric methylene diphenylene diisocyanate (mMDI), polymethylene polyphenylene polyisocyanate (pMDI) and a mixture of monomeric methylene diphenylene diisocyanate and polymethylene polyphenylene polyisocyanate (MDI), preferably selected from the group consisting of monomeric methylene diphenylene diisocyanate (mMDI) and a mixture of monomeric methylene diphenylene diisocyanate and polymethylene polyphenylene polyisocyanate (MDI).
35. The polyisocyanate of embodiment 34, wherein the monomeric methylene diphenylene diisocyanate (mMDI) comprises, preferably consists of, one or more 4,4'-methylene (diphenyl diisocyanate) (4,4'-MDI), 2,2'-methylene (diphenyl diisocyanate) (2,2'-MDI) and 2,4'-methylene (diphenyl diisocyanate) (2,4'-MDI), preferably 4,4'-methylene (diphenyl diisocyanate) (4,4'-MDI).

36. The polyisocyanate of any one of embodiments 31 to 35, having a NCO content in the range of from 10 to 60 weight-%, preferably in the range of from 20 to 55 weight-%, based on the total weight of the polyisocyanate.
37. The polyisocyanate of embodiment 36, having a NCO content in the range of from 25 to 35 weight-%, preferably in the range of from 30 to 35 weight-%, based on the total weight of the polyisocyanate.
38. The polyisocyanate of any one of embodiments 34 to 37, comprising a content of easily hydrolysable chlorine (EHC) of at most 500 mg/kg, preferably of at most 450 mg/kg, more preferably of at most 400 mg/kg, the EHC being preferably determined according to ASTM D4667-87.
39. The polyisocyanate of any one of embodiments 34 to 38, having a brightness value L* of at least 40, preferably in the range of from 40 to 100, more preferably in the range of from 45 to 99, more preferably in the range of 55 to 98, more preferably in the range of from 75 to 95, the brightness value L* being preferably determined according to ASTM D7133-16.
40. The polyisocyanate of embodiment 36, when the polyisocyanate is TDI, said polyisocyanate has a NCO content in the range of from 40 to 50 weight-%, preferably in the range of from 45 to 50 weight-%, based on the total weight of the polyisocyanate.
41. Use of at least one polyisocyanate R(—NCO)x, with x=2 or more, according to any one of embodiments 31 to 40 for preparing polyurethanes.
42. A chemical production unit for carrying out the process for preparing at least one polyisocyanate R(—NCO)x according to any one of embodiments 1 to 30, comprising
    - a reaction zone Z1 for preparing the at least one polyamines R(—$NH_2$)x, with x=2 or more, comprising
    - a reaction means for preparing a mixture R1;
    - a means for removing at least a portion P1 of the mixture R1 from the reaction zone Z1;
    - a storing device D1 for storing P1 for a period of time Δt1, wherein Δt1 is in the range of from 1 minute to 7 d;
    - a means for removing at least a portion P2 of P1, P2 comprising R(—$NH_2$)x, from D1;
    - a reaction zone Z2 for preparing the at least one polyisocyanate R(—NCO)x comprising
    - a reaction means for reacting P2 with phosgene and obtaining a mixture R2.

It is explicitly noted that the above set of embodiments represents a suitably structured part of the general description directed to preferred aspects of the present invention, and, thus, suitably supports, but does not represent the claims of the present invention.

In the context of the present invention, a term "X is one or more of A, B and C", wherein X is a given feature and each of A, B and C stands for specific realization of said feature, is to be understood as disclosing that X is either A, or B, or C, or A and B, or A and C, or B and C, or A and B and C. In this regard, it is noted that the skilled person is capable of transfer to above abstract term to a concrete example, e.g. where X is a chemical element and A, B and C are concrete elements such as Li, Na, and K, or X is a temperature and A, B and C are concrete temperatures such as 10° C., 20° C., and 30° C. In this regard, it is further noted that the skilled person is capable of extending the above term to less specific realizations of said feature, e.g. "X is one or more of A and B" disclosing that X is either A, or B, or A and B, or to more specific realizations of said feature, e.g. "X is one or more of A, B, C and D", disclosing that X is either A, or B, or C, or D, or A and B, or A and C, or A and D, or B and C, or B and D, or C and D, or A and B and C, or A and B and D, or B and C and D, or A and B and C and D.

The present invention is further illustrated by the following example 1 and FIGS. 1 and 2.

EXAMPLE

Example 1 Processes for Producing Polyisocyanates/Properties Comparison (Laboratory Experiments)

4,4'-Methylenedianiline (4,4'-MDA) was stored in the dark at two different temperatures, namely 140 and 170° C., for a total of 12 weeks in the absence of air. After various storage stages (0, 1, 4 and 12 weeks), part of the stored MDA sample was removed and converted to the corresponding isocyanate.

To do so, after each various storage stage, 100 g of MDA was dissolved in 1200 g of mono chlorobenzene (MCB) and metered into a stirred 2.7 L reactor over 1 hour at about 50° C., wherein a solution of 200 g of phosgene and 1200 g of MCB was placed under reflux. During the dosing, a suspension forms which clears up after heating up to 120° C.

After partial cooling, HCl, phosgene and parts of the solvent are removed from the mixture comprising methylene diphenyl diisocyanate (MDI) by evacuation.

After the aforementioned removal, the obtained mixture comprising MDI was drained off and filled into a rotary evaporator, where the solvent was separated off initially at 50 mbar and at 100° C. and later at 20 mbar and at 180° C. Further, a de-chlorination step is performed according to method well-known in the art, obtaining a MDI stream.

The NCO number, easily hydrolysable chlorine (EHC) and brightness values (L*) are determined from the resulting MDI samples (a-h). The EHC was determined according to ASTM D4667-87 and the brightness value L* being determined according to ASTM D7133-16. The values show a significant deterioration in the quality parameters, increase of EHC and decrease of L*, after just 1 week of exposure.

TABLE 1

| Samples | Storage time (Δt1)/ Storage T° C. | Brightness value L* | EHC (mg/kg) |
|---|---|---|---|
| a (Reference) | 0 h/140 | 62 | 130 |
| b (Reference) | 0 h/170 | 69 | 220 |
| c (Inventive) | 7 days/140 | 48 | 440 |
| d (Inventive) | 7 days/170 | 45 | 430 |
| e (Comparative) | 4 weeks/140 | 42 | 610 |
| f (Comparative) | 4 weeks/170 | 36 | — |
| g (Comparative) | 12 weeks/140 | 28 | 670 |
| h (Comparative) | 12 weeks/170 | 21 | 930 |

CITED LITERATURE

Figure 1:
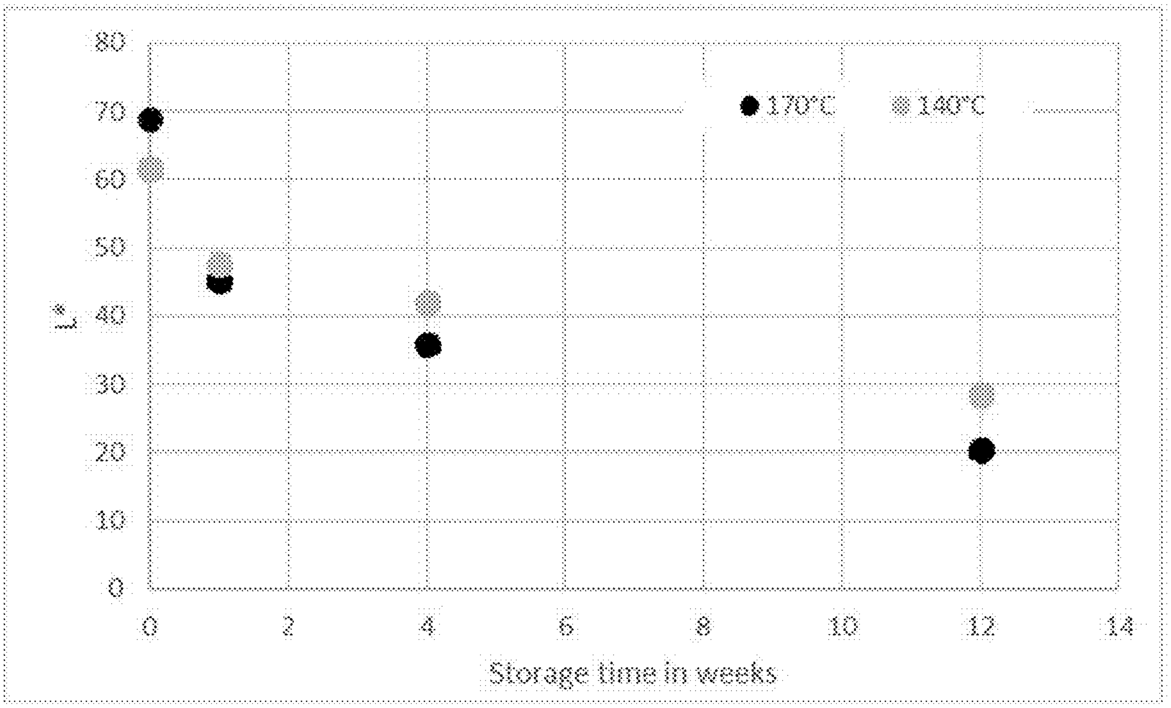
FIG. 1 shows the brightness value L* determined for the 4,4'-MDI obtained after various storage duration namely 0, 1, 4 and 12 weeks.
Figure 2:
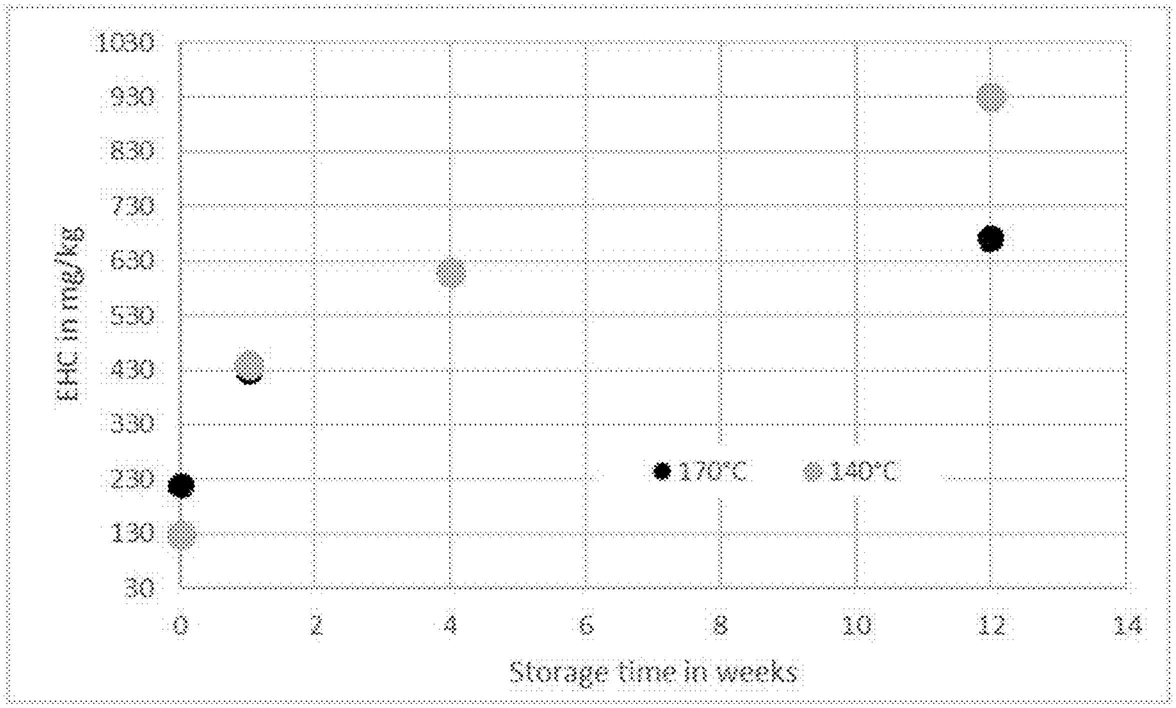
FIG. 2 shows the content of EHC determined for the 4,4'-MDI obtained after various storage duration namely 0, 1, 4 and 12 weeks.

U.S. Pat. No. 4,847,408 B
US 2004/0260117 A1
EP 2 912 010 B1
U.S. Pat. No. 8,436,204 B2
WO 2013/060836 A
WO 2013/079517 A

The invention claimed is:

1. A process for preparing at least one polyisocyanate R(—NCO)x, the process comprising (i) preparing a mixture R1 comprising at least one polyamine R(—$NH_2$)x, with x=2 or more, in a first reaction zone Z1;

(ii) passing at least a portion P1 of the mixture R1, P1 comprising R(—$NH_2$)x, into a storing device D1 and storing P1 in D1 for a period of time Δt1;

(iii) removing, after storing for Δt1, at least a portion P2 of P1, P2 comprising R(—$NH_2$)x, from D1; passing P2 into a reaction zone Z2; and reacting, in Z2, R(—$NH_2$)x comprised in P2 with phosgene, obtaining a mixture R2 comprising the at least one polyisocyanate R(—NCO)x;

wherein Δt1 is in the range of from 1 minute to 7 days, and wherein the pressure in the storing device D1 is in the range of from 0.5 to 2 bar (abs).

2. The process of claim 1, wherein the at least one polyamine R(—$NH_2$)x is selected from the group consisting of monomeric methylene diphenylene diamine (mMDA), polymethylene polyphenylene polyamine (pMDA), a mixture of monomer methylene diphenylene diamine and polymethylene polyphenylene polyamine (MDA), tolylenediamine (TDA), isomers of xylylenediamine (XDA), isomers of diaminobenzene, 2,6-xylidine, naphthylene-1,5-diamine (1,5-NDA), 1,4-diaminobutane, 1,5-diaminopentane (PDA), 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4 (or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4 (3)-aminomethylcyclohexane (AMCA), 1,3-bis(aminomethyl) cyclohexane, 1,4-bis(aminomethyl)cyclohexane, bis(aminomethyl)norbornane (NBDA), 4,4'-diaminodicyclohexylmethane, 2,4'-diaminodicyclohexylmethane, triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl)hexane, and 1,3,5-tris(aminomethyl)cyclohexane.

3. The process of claim 1, wherein (i) comprises (i.1) reacting primary amines with an aldehyde compound in presence of an acid in a first reaction zone Z1, obtaining a mixture R0 comprising the primary amines and at least one polyamine R(—$NH_2$)x, with x=2 or more;

(i.2) separating the primary amines from the at least one polyamine R(—$NH_2$)x comprised in the mixture R0 obtained in (i.1), obtaining a mixture R1 comprising at least one polyamine R(—$NH_2$)x.

4. The process of claim 1, wherein storing P1 in D1 according to (ii) is performed in the dark.

5. The process of claim 1, wherein storing P1 in D1 according to (ii) is performed under a gas atmosphere, the gas atmosphere being an inert gas.

6. The process of claim 1, wherein, in D1, a temperature of a liquid phase of P1, T(P1), in ° C., is above the melting point of the at least one polyamine R(—$NH_2$)x comprised in P1, M(P1), in ° C.

7. The process of claim 6, wherein M(P1) is 80° C., and, in D1, T(P1)≥85° C.

8. The process of claim 6, wherein, when the at least one polyamine R(—$NH_2$)x is TDA, M(P1) is 100° C., and, in D1, T(P1)≥105° C.

9. The process of claim 1, wherein Δt1 is in the range of from 15 minutes to 6 days.

10. The process of claim 1, wherein reacting, in Z2, the at least one polyamine R(—$NH_2$)x comprised in P2 with phosgene according to (iii) comprises admixing a solvent to the at least one polyamine R(—$NH_2$)x comprised in P2 and stirring, obtaining a polyamine mixture;

contacting the polyamine mixture with phosgene in the reaction zone Z2 and heating the obtained mixture to a temperature in the range of from 90 to 140° C., obtaining the mixture R2.

11. Polyisocyanate R(—NCO)x, with x=2 or more, obtained according to a process according to claim 1 for use in a process for preparing polyurethanes.

12. The polyisocyanate of claim 11, having a brightness value L* of at least 40.

13. Use of at least one polyisocyanate R(—NCO)x, with x=2 or more, according to claim 11 for preparing polyurethanes.

14. A chemical production unit for carrying out the process for preparing at least one polyisocyanate R(—NCO)x according to claim 1, comprising a reaction zone Z1 for preparing the at least one polyamines R(—$NH_2$)x, with x=2 or more, comprising a reaction means for preparing a mixture R1;

a means for removing at least a portion P1 of the mixture R1 from the reaction zone Z1;

a storing device D1 for storing P1 for a period of time Δt1, wherein Δt1 is in the range of from 1 minute to 7 d;

a means for removing at least a portion P2 of P1, P2 comprising R(—$NH_2$)x, from D1;

a reaction zone Z2 for preparing the at least one polyisocyanate R(—NCO)x comprising a reaction means for reacting P2 with phosgene and obtaining a mixture R2.

* * * * *